United States Patent [19]
Zadehkoochak et al.

[11] Patent Number: 5,465,730
[45] Date of Patent: Nov. 14, 1995

[54] ELECTRICAL IMPEDANCE TOMOGRAPHY

[75] Inventors: Mohsen Zadehkoochak, Marlow; Barry H. Blott, Southampton; Geoffrey J. Daniell, Nr Romsey, all of England

[73] Assignee: British Technology Group Ltd., London, United Kingdom

[21] Appl. No.: 185,855

[22] PCT Filed: Jul. 24, 1992

[86] PCT No.: PCT/GB92/D1371
§ 371 Date: Jan. 25, 1994
§ 102(e) Date: Jan. 25, 1994

[87] PCT Pub. No.: WO93/02617
PCT Pub. Date: Feb. 18, 1993

[30] Foreign Application Priority Data

Jul. 26, 1991 [GB] United Kingdom ............ 9116215

[51] Int. Cl.$^6$ ........................................ A61B 5/05
[52] U.S. Cl. ........................ 128/734; 364/413.15
[58] Field of Search ....................... 128/734, 735, 128/741; 364/413.02, 413.13, 413.15

[56] References Cited

U.S. PATENT DOCUMENTS 4,617,939 10/1986 Brown et al. ............... 128/734
5,272,624 12/1993 Gisser et al. ............... 128/734

OTHER PUBLICATIONS

Geophysics, vol. 38, No. 6, 1973, pp. 1088–1108, J. R. Inman et al. "Resistivity Inversion" cited in the application—see p. 2.

Medical Physics, vol. 16, No. 2, 1989, New–York (US), pp. 162–169, D. C. Barber "a review of image reconstruction techniques for electrical impedance tomography"* see section VI : "Reconstruction Algorithms"*.

G. H. Golub et al., "Handbook Series Linear Algebra", Singular Value Decomposition and Least Squares Solutions, Numer. Math 14, 1970, pp. 403–420.

C. C. Barber et al., "Imaging Spatial Distributions of Resistivity Using Applied Potential Tomography", Electronics Letters, 27 Oct. 1983, vol. 19 No. 2, pp. 933–935.

M. Zadehkoochak et al., "A Transputer Implemented Algorithm for Electrical Impedance Tomography", Institute of Physical Sciences in Medicine, 1990 vol. 11 No. 3, pp. 223–230.

C. J. Korre, "A Sensitivity Coefficient Method for the Reconstruction of Electrical Impedance Tomograms", Clin. Phys. Physiol. Med., 1989, vol. 10 No. 3, pp. 275–281.

T. J. Yorkey, "Comparing Reconstruction Methods for EIT", Ph.D. Thesis, University of Wisconsin (Madison) 1986, pp. 104–123.

*Primary Examiner*—Max Hindenburg
*Attorney, Agent, or Firm*—Cushman, Darby & Cushman

[57] ABSTRACT

The invention provides a method, and apparatus for practicing the method, of producing an electrical impedance tomographic image of an object, comprising the steps of: positioning a plurality of electrodes peripherally of the object in electrical contact therewith, repeatedly applying an electrical signal between at least two selected ones of the electrodes to which the electrical signal is applied being different for different applications of the signal, registering the measured electrical potentials as measured data obtained during a plurality of different applications of the applied electrical signa, and processing the measured data to provide data defining the electrical impedance tomographic image of the object. Characterized in that the processing of the measured data is effected by the use of spectral expansion of a matrix representation of the sensitivity of the measurement process to an a priori assumed approximation of the object to provide data defining a series of mutually orthogonal component or basis images.

6 Claims, 5 Drawing Sheets

ELECTRICAL IMPEDANCE TOMOGRAPHY

FIELD OF THE INVENTION

This invention relates to electrical impedance tomography (EIT). EIT is a relatively recently developed imaging technique which can be used for medical purposes and is capable of producing tomographic images of changes in the spatial distribution of conductivity within a body segment. This is clinically useful, since these variations are brought about by physiological changes occurring in the body, such as lung ventilation, blood flow and gastric emptying.

DESCRIPTION OF RELATED ART

In such medical use of the technique, an alternating current, typically of some 5 mA at a frequency of about 50 kHz, is injected via two or more of, say sixteen standard electrodes spaced around the body segment. The potential at the remaining electrodes is sampled and passed to a computer for further analysis. The technique offers several advantages such as a fast data collection rate and a relatively low cost of the equipment. It is also safe and non-invasive and can be used for continuous monitoring.

Developments in this field can be categorized broadly into instrumentation (hardware) and image reconstruction (software). The former addresses the problems associated with data collection and the latter is concerned with producing images from the data.

Although, strictly speaking, the problem of image reconstruction is non-linear, it is now well established that even linear methods of reconstruction are capable of producing clinically useful, although perhaps non-optimal, images.

The problem of reconstructing, from the measured date, an image representing the nonuniform distribution of conductivity over a body segment is, in effect, the inverse of the simpler problem of calculating what the measured data would be if the conductivity distribution were known, and various algorithms for treating the data to solve the inverse problems have already been proposed: for example a method based on the concept of back-projection, due to Barber and his collaborators at the University of Sheffield, England, is disclosed and discussed in U.S. Pat. No. 4617939 and in their paper (Imaging spatial distributions of resistivity using applied potential tomography: Barber D. C., Brown B. H. and Freeston I. L. in Electronic Letters (1983) 19 (22), 933–5), and an iterative method due to Kotre is described in another paper (A sensitivity coefficient method for the reconstruction of electrical impedance tomograms: Kotre C. J., in *Clin. Phys. Physio. Meas.* (1989) 10, 275–81).

In the wider mathematical context, a known method of approaching inverse problems of this general kind is the method of spectral expansion, and this method has indeed been applied to the solution of practical problems in the field of geophysics as described in a paper by Inman J. R., Ryu J. and Ward S. H. entitled "Resistivity Inversion" published in Geophysics (1973) 38 (6), 1088–108. Spectral expansion has also been used as a means of analyzing at least one of the known methods (Kotre's) of reconstructing an electrical impedance tomographic image, but it has not hitherto been proposed to employ spectral expansion directly in the process of reconstructing a tomographic image of an object by the method of electrical impedance tomography. However, it is now perceived that the technique of spectral expansion may be so employed with considerable advantage.

SUMMARY OF THE INVENTION

It is an object of the resent invention to provide an improvement in the reconstruction of images produced by the use of EIT, and this object is achieved according to the invention by the application of spectral expansion techniques in the reconstruction of EIT images.

According to the invention, therefore, a method of producing an electrical impedance tomographic image of an object is provided, comprising the steps of: positioning a plurality of electrodes peripherally of the object in electrical contact therewith, repeatedly applying an electrical signal between at least two selected ones of the electrodes and measuring the resulting electrical potentials at others of the electrodes, the selection of electrodes to which the electrical signal is applied being different for different applications of the signal, registering the measured electrical potentials as measured data obtained during a plurality of different applications of the applied electrical signal, and processing of the measured data is effected by the use of spectral expansion of a matrix representation of the sensitivity of the measurement process to an a priori assumed approximation of the object to provide data defining a series of mutually orthogonal component or basis images and by deriving from the measured data relative weightings in accordance with which some or all of the basis images are to be combined to provide a reconstructed image constituting the electrical impedance tomographic image of the object.

Usually, the electrodes will be equally spaced around the periphery of the object and the applied signal will be applied successively to each pair of mutually adjacent electrodes and at each application of the signal between a particular pair of electrodes the potentials of all the other electrodes, relative to one another, will be measured.

If there are a total of sixteen electrodes, fourteen potentials will be measured each time, yielding thirteen potential differences relative to one potential which must be regarded as a reference for the others; and application of the applied signal to each in turn of the possible sixteen pairs of mutually adjacent electrodes will produce a total of 16×13 or 208 potential differences. However, if two pairs of mutually adjacent electrodes are considered, it will be seen that applying the applied signal to one pair will produce the same potential difference across the other pair as is produced across the one pair by applying the applied signal across the other pair. Thus, the 208 potential differences obtained represent only 104 independent items of measured data.

BRIEF DESCRIPTION OF THE DRAWINGS

The invention, employing spectral expansion, will be further explained in the following description with reference to the accompanying drawings, in which.

DESCRIPTION OF THE PREFERRED EMBODIMENTS

Figure 1B:
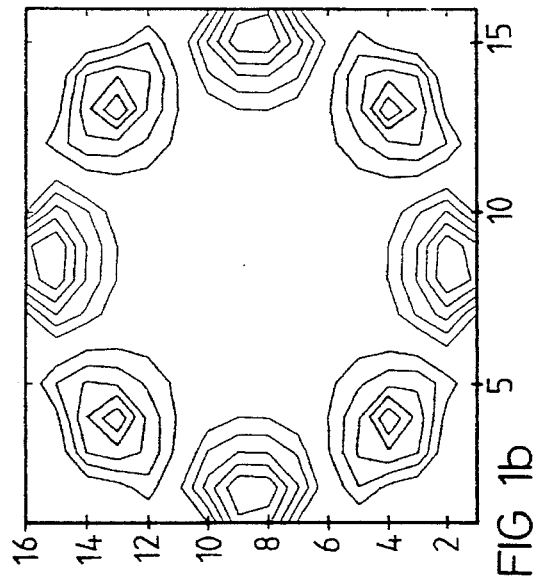
FIGS. 1a, 1b, 1c and 1d show four of a series of basis images which may be derived by spectral expansion from a Jacobian, or matrix, representation of the sensitivity of the measurement process to the a priori assumed distribution of electrical resistivity of a section through an object of which a reconstructed image is to be produced.
Figure 1D:
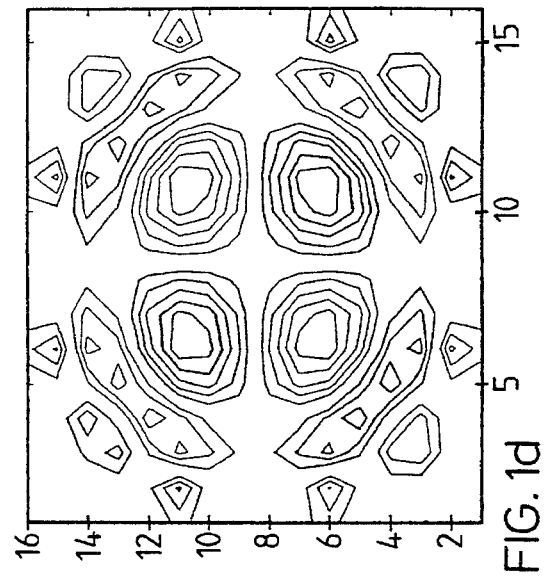

The method of spectral expansion enables the solution to the problem of EIT (i.e. the image, x) to be expanded into a set of n mutually orthogonal component or basis images, where n is equal to the number of independent measurements (n-104 for 16 electrodes):

$$x = \sum_{i=1}^{n} a_i x_i \quad (1)$$

Two useful properties of this approach are:

i) The basis images $x_u$ are mutually orthogonal so that each of them potentially contains different information about the final reconstructed image.

ii) The coefficients $a_i$ are derived from the measured data, and the associated uncertainties, which are determined by the data noise, are easily calculated and can be used to regularize the image by excluding from the solution, or giving less emphasis to, those basis images that are most sensitive to data noise, i.e. those with large uncertainty in their coefficients. This has consequences in terms of the image noise versus resolution trade-off.

In carrying out the method, the Jacobian (or sensitivity) matrix J is first calculated using for example the compensation theorem as discussed in the 1986 Ph.D thesis of T. J. Yorkey, University of Wisconsin at Madison, USA, entitled "Comparing Reconstruction Methods for Electrical Impedance Tomograpy". Briefly, the Jacobian matrix J describes what changes are to be expected in the measurements made at the electrodes as a result of resistivity changes at "pixels" in the object under examination, and the problem to be solved is then to find the inverse of this relation so that the pixel values for the corresponding reconstructed image may be derived from the measurements actually made at the electrodes. J is an m by n matrix, where m is the number of pixels which the reconstructed image is to contain and n is as above defined, and can be decomposed such that:

$$J = U E V^T \quad (2)$$

where U is m by m and the columns of U are the eigenvectors of $JJ^T$, V is n by n and the columns of v are the eigenvectors of $J^T J$, and E is m by n and is a 'diagonal' matrix whose non-zero elements are the positive square roots of the eigenvalues of $JJ^T$ (or $J^T J$). Decomposition of J in accordance with equation (2) is discussed in a paper by G. H. Golub and C. Reinsch entitled "Singular Value Decomposition and Least Squares Solutions" (Numer, Math. (1970) 14, 403–420), and conveniently can be carried out in practice using the singular value decomposition technique provided in the mathematical analysis package MATLAB available from the MathWorks Inc.

The columns of V form the basis images ($x_i$ in Equation (1)). The columns of U specify how the measured data should be combined to produce the coefficients $a_i$. The diagonal elements of $\gamma$, the set of which is called the spectrum of the problem, indicate how much the basis image coefficients are affected by the data noise. They are ordered in decreasing magnitude. Large elements are associated with well defined basis images (i.e. those which are least susceptible to data noise).

Having decomposed the sensitivity matrix in this way, its minimum 2-norm least squares inverse R can be written, thus:

$$R = V \gamma^{-1} U^T \quad (3)$$

where elements of $\gamma^{-1}$ are given by:

$$\Sigma_i^{-1} = \begin{bmatrix} \frac{1}{\Sigma_i} \text{ if } \Sigma_i > O \\ O \text{ if } \Sigma_i = O \end{bmatrix} \quad (4)$$

Because EIT image reconstruction is an ill-conditioned problem, a generalized solution as given by Equation (3) is of little or no value. The difficulty arises because some of the diagonal elements of $\gamma$ (whose squares are the eigenvalues) are much smaller than others and according to Equation (3) utilizing them in reconstruction results in the data noise propagating through to the image in its amplified form. Ways to control this are known as regularization methods. One such method is to construct the inverse out of only those eigenvectors corresponding to the largest eigenvalues. This is equivalent to considering the small eigenvalues to be zero. This method is known as regularization by truncated singular value decomposition (SVD). More generally, it is possible to introduce a regularization matrix F, such that:

$$R = V F \gamma^{-1} U^T \quad (5)$$

and by choosing F to be diagonal its elements can be interpreted as scaling factors for the coefficients of the basis images. Two special cases are to be noted for the generalized (unregularized) solution, F is the unit matrix and for truncated SVD, F is a 'truncated' unit matrix which has some of its diagonal elements replaced by zero.

In general it is found empirically that the noisy basis images are those which possess high spatial frequency components, and the exclusion of the noisy basis images therefore results in a degradation of the resolution; hence there is a trade-off between resolution and the noise in the solution.

Ordering the basis images in decreasing magnitude of their associated eigenvalues gives some rather interesting insights into the problem. For example, it is seen that the basis images best defined by the data (i.e. those with large eigenvalues and therefore least affected by data noise) have predominant features around the periphery of the uniform image domain.

Figure 1A:
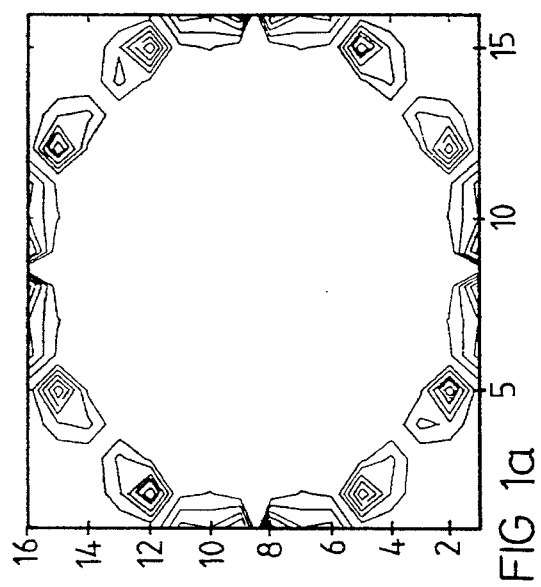
Figure 1C:
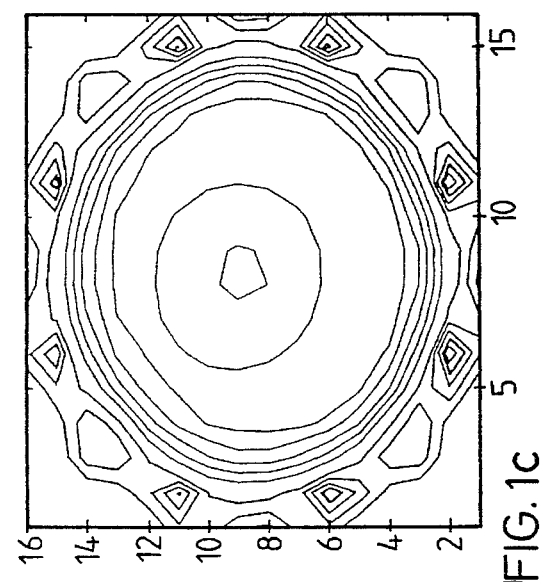
Figure 2A:
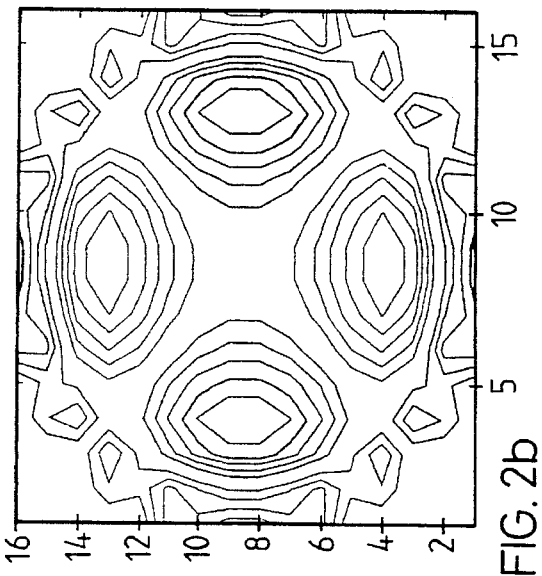
FIGS. 2a, 2b, 2c and 2d show four further examples of basis images from the same series as those shown in FIG. 1.
Figure 2B:
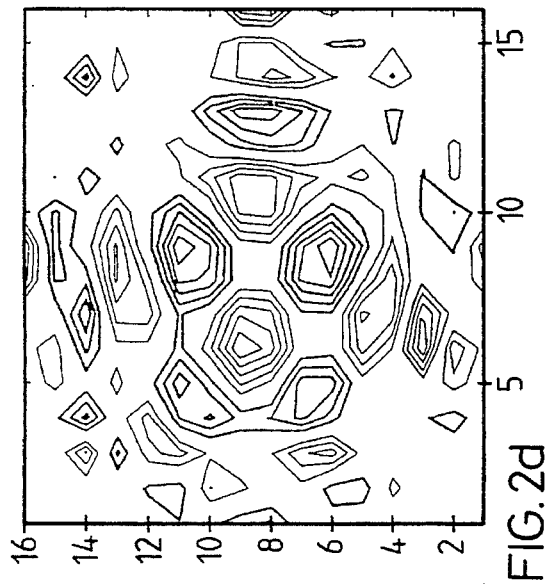
Figure 2C:
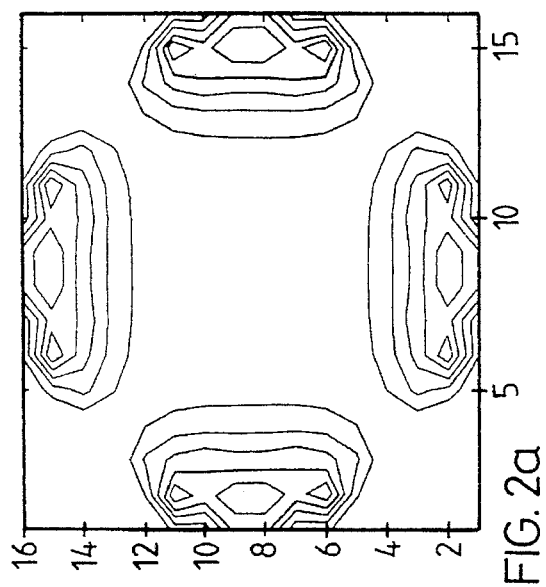
Figure 2D:
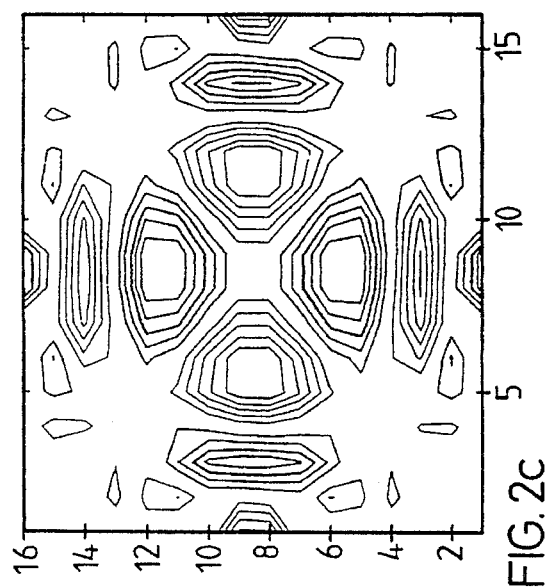

From the complete set of the basis images, subsets can be selected to illustrate either the specific characteristics of the basis images or the development of structure with particular symmetries. For example FIGS. 1a, 1b, 1c and 1d of the accompanying drawings illustrates the variation in the structure at peripheral and central positions in the image as the basis image index increases. It is particularly noticeable that the first basis image, which is shown in FIG. 1a has all the structure very close to the periphery, where the current density is highest when measurements are being made. FIG. 1b shows the 18th basis image, which has peripheral features slightly away from the electrodes and shows a corresponding degradation in the resolution.

In the center of the image, the lowest spatial frequency does not appear until basis image number 25 (FIG. 1c), which has a rather wide and low-resolution circular feature. Basis images with more structure in the center appear later in the series (FIG. 1d) shows the 49th basis image), and are consequently more susceptible to data noise.

FIGS. 2a, 2b, 2c and 2d of the drawings show basis images numbers 10, 31, 50 and 70 which have two-fold symmetry along the x or y axes, and illustrate the development of radial structure as the basis image index increases. FIGS. 2a–2d clearly demonstrate that more random variation into the image elements since, as before, the basis images with higher index numbers are more susceptible to data noise.

It may be demonstrated that the known iterative methods of processing the measured data to derive an image therefrom, such as those of Kotre (referred to above) and of Kaczmarz, allow the adjustment of the noise versus resolution trade-off by varying the number of iterations. Although that approach provides some choice it is still somewhat limited, and application of the method of spectral expansion in accordance with the invention enables a more flexible approach to be taken since it allows complete freedom as to which basis images to include in solution from a complete set of 104. Furthermore, by appropriate choice of the regularization matrix F different weightings can be given to the basis images which make up the solution. It is not profitable to attempt to provide a general definition or specification of how these choices are to be made: they are matters for judgement in each particular set of circumstances, since they will depend on various factors such as the amount of data noise and also, possibly, the expected image configuration. Also, for a different (i.e. not uniform) starting resistivity distribution a different set of basis images is generated, with different eigenvalues, as will be further illustrated below.

Preliminary results obtained by use of the invention confirm previous findings that for reconstruction proposes there is no best combination of basis images for all occasions, because of the noise versus resolution trade-off. It is found, for example, that using too few basis images results in distorted and non-representative images.

Mention has been made above of the already known use of the Kaczmarz inversion method of deriving electrical impedance tomographic images, and it is instructive by way of comparison to make use of spectral expansion in order to analyze the regularization properties of the Kaczmarz method (as to which, reference is made to *Clin. Phys. Physiol. Meas.*, (1990), I1, 223–230: "A transputer implemented algorithm for electrical tomography") as will now be described.

First, Equation 5 above may be rearranged to obtain an expression for F:

$$F = V^T R U \gamma \quad (6)$$

The method 9of Kaczmarz is an iterative method which generates a different reconstruction matrix after each iteration. To analyze the regularization property of these matrices, F may be calculated according to Equation 6. Iterations 1, 7, 12 and 20 may be chosen as typical examples. The corresponding regularization matrices are designated $F_1$, $F_7$, $F_{21}$ and $F_{20}$ respectively. In each case the regularization matrix was found to be predominantly diagonal. This suggests that the diagonal elements of F can be directly interpreted as scaling factors for the coefficients $a_i$.

Figure 3:
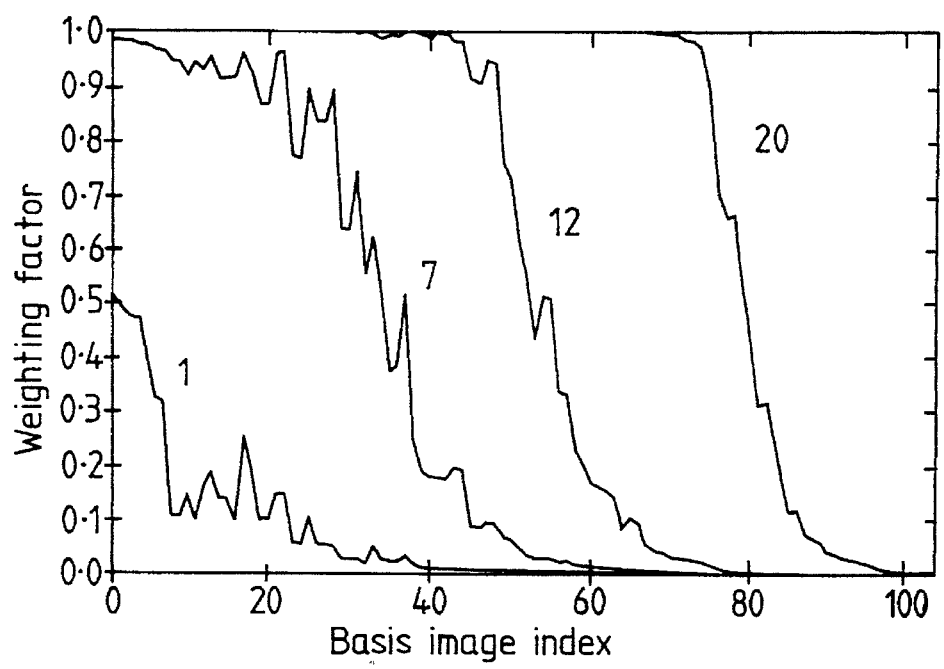
FIG. 3 shows graphically how various combinations or selections of the basis images may be combined, with various weightings, to provide a reconstructed image having greater resolution at the expense of greater noise.

FIG. 3 of the drawing shows a plot of the diagonal elements of $F_1$, $F_7$, $F_{21}$ and $F_{20}$. This analysis clearly confirms the regularization properties of the Kaczmarz method which have been independently determined experimentally. The following points may be noted:

i) As more iterations are carried out, the number of basis images (as derived by spectral expansion) included in the solution increases, tending towards the inclusion of all basis images as the number of iterations tends to infinity.

ii) The graphic representation shown in FIG. 3 confirms the proposition that, in the Kaczmarz method, the basis images with large eigenvalues are well represented by the early iterations and that those with small eigenvalues appear only in the later stages of the process. Thus regularization can be achieved by terminating the iterative procedure after a finite number of iterations.

Figure 4:
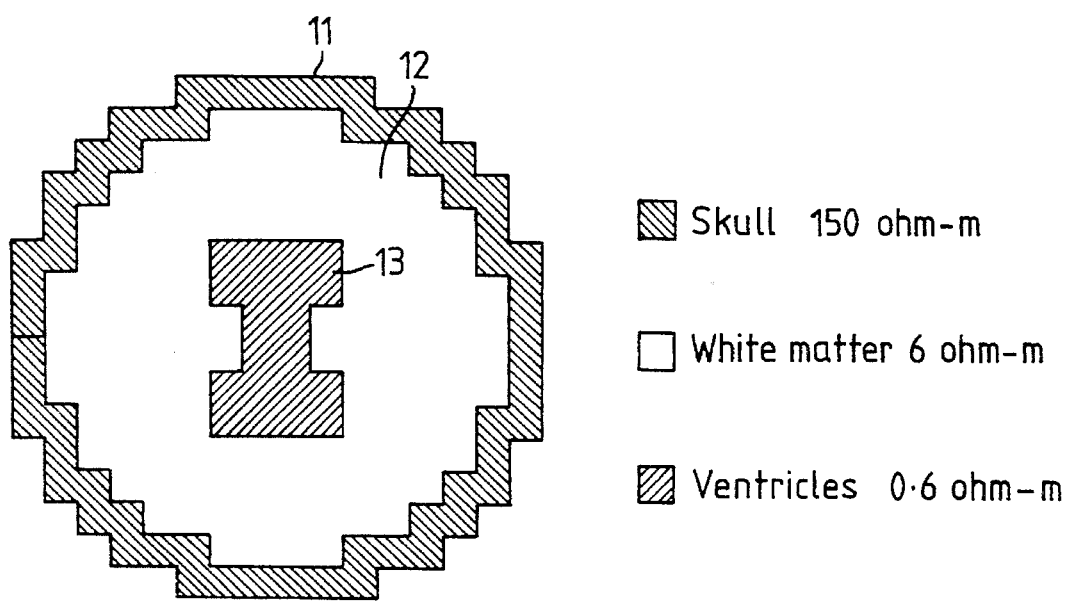
FIG. 4 shows a representation in "pixels" of a markedly non-uniform a priori assumed distribution of resistivity which may be used for calculating the Jacobian matrix which will be used in reconstructing a tomographic image of a human head by the method according to the invention.
Figure 5A:
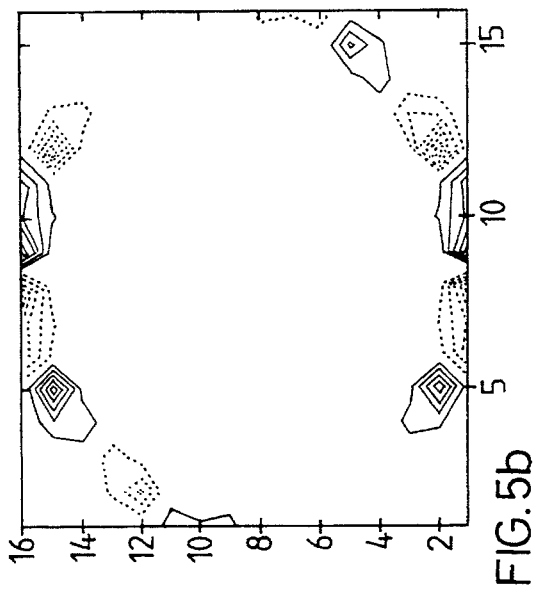
FIGS. 5a, 5b, 5c and 5d show the first four of the series of basis images obtained by spectral expansion from a model having the same outline as that shown in FIG. 4 but having completely uniform resistivity within that outline.
Figure 5B:
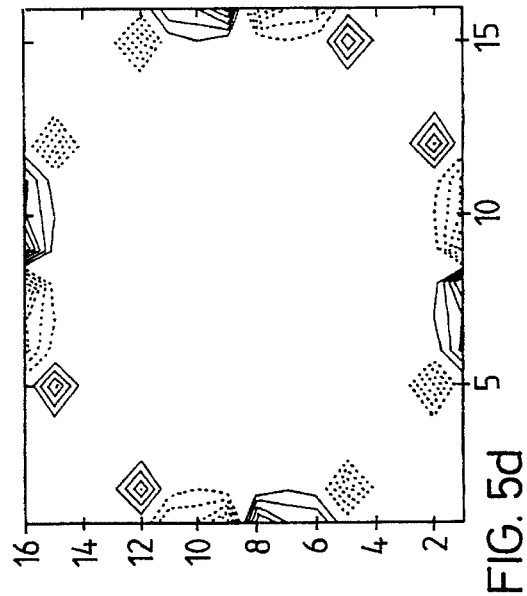
Figure 5C:
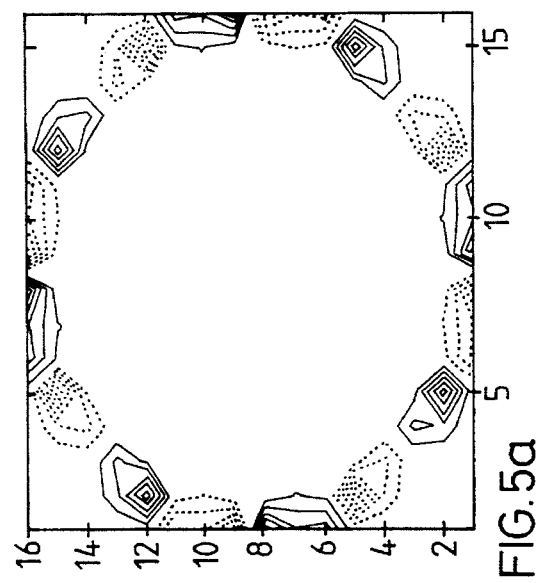
Figure 5D:
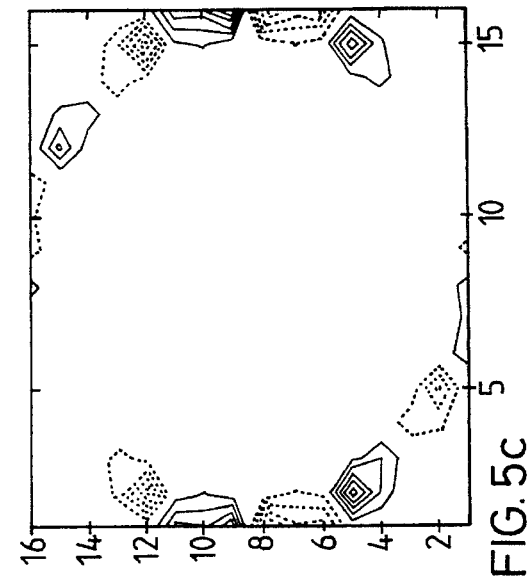
Figure 6A:
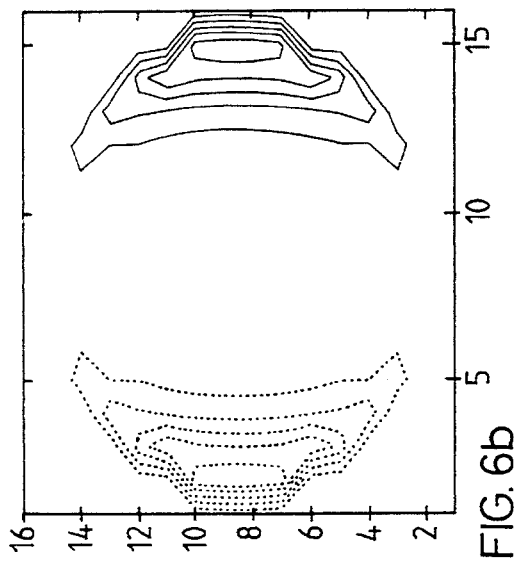
FIGS. 6a, 6b, 6c and 6d show, for comparison, the first four basis images from the series which is derived by spectral analysis from the Jacobian representing the distribution of resistivity shown in FIG. 4.
Figure 6B:
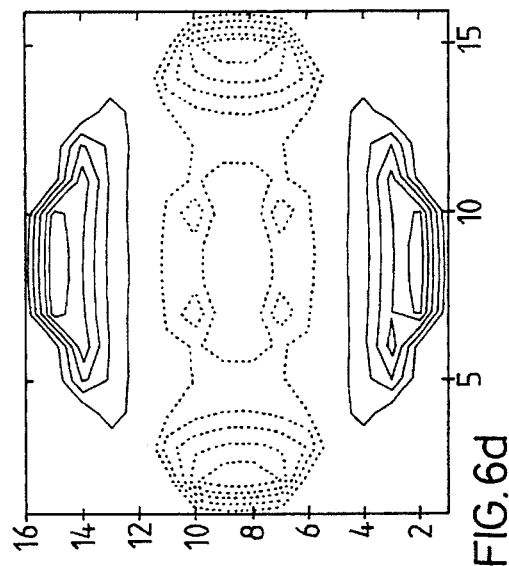
Figure 6C:
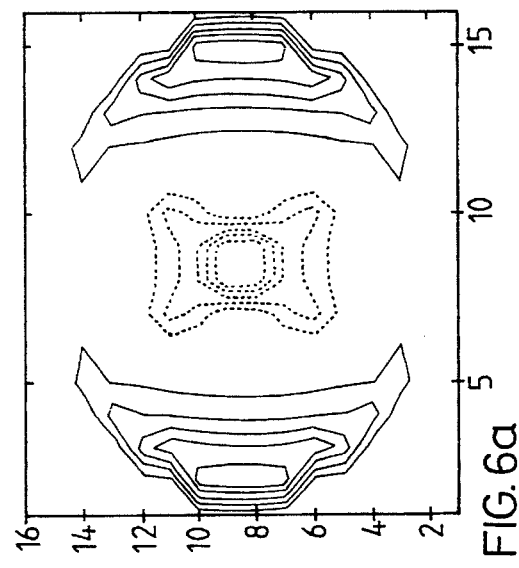
Figure 6D:
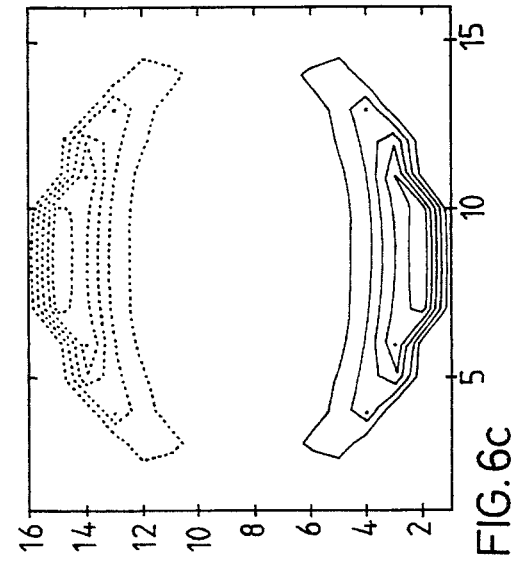

In the foregoing it has been explicitly or implicitly assumed that the image being reconstructed is of a circular original object which is of almost uniform electrical resistance with only minor local perturbations, and that this is interrogated by applying an electrical signal between two adjacent electrodes of several which are spaced around the object and measuring the potentials arising at the remaining electrodes; but the method is equally applicable to nonhomogeneous object domains of other geometries, and to other measurement strategies. By way of illustration of use of the method in connection with an object with a notably non-uniform resistivity distribution, an approximate model of human head was constructed on a 16 by 16 net as shown in FIG. 4 of the accompanying drawings, with regions 11, 12 and 13 respectively representing the skull, white matter of the brain and its ventrices and assumed to have resistivities in the ratios 25:1:0.1. Results from this model and from another, having the same outline but completely uniform resistivity, were then compared.

FIGS. 5a, 5b, 5c and 5d show the first four basis images obtained, for the uniform resistivity case, by applying the spectral expansion method. It can be seen that these basis images show features only near the periphery of the image domain, which could have been expected bearing in mind that current densities are most intense in this region and result in relatively high sensitivity there. The images of FIGS. 5a to 5d are to be compared with the corresponding first four basis images for the head model shown in FIG. 4, which are shown in FIGS. 6a, 6b, 6c and 6d. It will be seen that the latter show a marked increase in sensitivity nearer the center of the image domain. In FIGS. 5a–5d and 6a–6d, the solid lines show positive values of resistivity whilst the dotted lines show negative values.

Ordering the basis images in decreasing magnitude of their associated eigenvalues gives some rather interesting insights into the problem. For example, it is seen that the basis images best defined by the data (i.e. those with large eigenvalues and therefore least affected by data noise) have predominant features around the periphery of the image domain for the case of a uniform resistivity distribution.

The lowest spatial frequency does not appear in the center until basis image number 25 which has a rather wide and low resolution circular feature. Basis images with more structure in the center appear later in the series and are consequently more susceptible to data noise.

It has been shown how various existing algorithms can be analyzed by the method of spectral expansion, to reveal how their modes of operation correspond implicitly to particular ways of choosing a strategy for selecting which of a set of basis images provided by spectral expansion to include in a reconstructed image and choosing a regularization matrix by means of which different weightings will be given to the basis images which make up the solution. Results obtained confirm that there is no global best combination of basis images for reconstruction proposes because of the noise versus resolution trade-off. This trade-off can be directly interpreted in terms of the number of basis images used to make up the image keeping in mind that using too few basis images results in a distorted image overall. Use of the spectral expansion method directly, in accordance with the invention, to derive explicitly a set of basis images which are then available for combination, has the advantage, over previously known methods of deriving an EIT image, that it leaves the practitioner with maximum width of choice as to the way in which the basis images should be combined to form the reconstructed image.

What is claimed is:

1. A method of producing an electrical impedance tomographic image of an object, comprising the steps of:

positioning a plurality of electrodes peripherally of the object in electrical contact therewith;

applying an electrical signal between the ones of the plurality of electrodes of a group of at least two selected ones of the plurality of electrodes and measuring respective resulting electrical potentials at the ones of the plurality of electrodes other than the group of selected ones;

successively repeating the step of applying an electrical signal, selecting the group of at least two selected ones of the plurality of electrodes to be different ones of said plurality of electrodes for each successively repeated step of applying an electrical signal;

registering the measured respective electrical potentials as measured data obtained during each of a plurality of different applications of the electrical signal; and processing the measured data to provide data defining an electrical impedance tomographic image of the object comprising the steps of:

using a spectral expansion of a matrix representation of a sensitivity of a measurement process of an a priori assumed approximation of the object to provide data defining a series of mutually orthogonal basis images, and deriving from the measured data relative weightings in accordance with which at least some of the basis images are to be combined to provide a reconstructed image constituting the electrical impedance tomographic image of the object.

2. A method as claimed in claim 1, further comprising the step of distributing the electrodes peripherally around the object, wherein the step of repeatedly applying the electrical signal includes the steps of applying the electrical signal successively to different pairs of mutually adjacent ones of said plurality of electrodes, and said measuring of said respective electrical potentials includes a measurement made at each of said plurality of electrodes to which the applied signal is not being applied.

3. A method as claimed in claim 1 or 2, wherein said step of using a spectral expansion of a matrix representation includes the step of applying spectral expansion to a Jacobian matrix representing the sensitivity of the measurement process to the a priori assumed uniform distribution of resistivity across the object to be imaged.

4. A method as claimed in claim 1 or 2, wherein said step of using a spectral expansion of a matrix representation includes the step of applying spectral expansion to a Jacobian matrix representing the sensitivity of the measurement process to a predetermined assumed non-uniform distribution of resistivity across the object to be imaged.

5. A method as claimed in claim 2, further comprising the step of choosing and applying a strategy of determining which basis images are combined, and with what weighting, to provide the reconstructed image.

6. Apparatus for producing an electrical resistance tomographic image of an object, comprising a plurality of electrodes for positioning peripherally around the object and in electrical contact therewith;

means for applying an electrical signal between the ones of the plurality of electrodes of a group of at least two selected ones of the plurality of electrodes and measuring respective resulting electrical potentials at the ones of the plurality of electrodes other than the group of selected ones;

means for registering the measured respective electrical potentials as measured data obtained during each of a plurality of different applications of the electrical signal; and data processing means for processing the measured data to provide data defining an electrical impedance tomographic image of the object by a spectral expansion to derive data defining a series of mutually orthogonal basis images to derive from the measured data relative weightings in accordance with which at least some of the basis images are to be combined to provide a reconstructed image constituting the electrical impedance tomographic image of the object.

* * * * *